United States Patent
Chen et al.

(10) Patent No.: US 10,247,800 B2
(45) Date of Patent: Apr. 2, 2019

(54) MRI PULSE SEQUENCE DESIGN

(71) Applicant: Siemens Healthcare GmbH, Erlangen (DE)

(72) Inventors: Xiao Chen, Princeton, NJ (US); Mariappan S. Nadar, Plainsboro, NJ (US); Benjamin L. Odry, West New York, NJ (US); Boris Mailhe, Plainsboro, NJ (US)

(73) Assignee: Siemens Healthcare GmbH, Erlangen (DE)

(*) Notice: Subject to any disclaimer, the term of this patent is extended or adjusted under 35 U.S.C. 154(b) by 105 days.

(21) Appl. No.: 15/655,936

(22) Filed: Jul. 21, 2017

(65) Prior Publication Data

US 2019/0025392 A1  Jan. 24, 2019

(51) Int. Cl.
*G01R 33/54* (2006.01)
*A61B 5/055* (2006.01)
*G01R 33/56* (2006.01)
*G01R 33/563* (2006.01)
*A61B 5/00* (2006.01)

(52) U.S. Cl.
CPC ........... *G01R 33/543* (2013.01); *A61B 5/055* (2013.01); *A61B 5/7264* (2013.01); *G01R 33/5608* (2013.01); *G01R 33/56341* (2013.01); *G01R 33/56366* (2013.01)

(58) Field of Classification Search
CPC ............ G01R 33/543; G01R 33/5608; G01R 33/56341; G01R 33/56366; A61B 5/055; A61B 5/7264
See application file for complete search history.

(56) References Cited

U.S. PATENT DOCUMENTS

| 8,723,518 B2 | 5/2014 | Seiberlich et al. |
| 2015/0301147 A1* | 10/2015 | Gulani ............ G01R 33/56563 324/309 |
| 2015/0302297 A1 | 10/2015 | Griswold et al. |
| 2017/0007148 A1* | 1/2017 | Kaditz .................. A61B 5/055 |

OTHER PUBLICATIONS

Ontaneda, D. et al., "Magnetic Resonance Fingerprinting: A New Window into Multiple Sclerosis," https://consultqd.clevelandclinic.org/2016/09/magnetic-resonance-fingerprinting-new-window-multiple-sclerosis/ , Sep. 26, 2016.

* cited by examiner

*Primary Examiner* — Gregory H Curran

(57) ABSTRACT

A method uses an artificial neural network (ANN) to automatically produce a magnetic resonance (MR) pulse sequence. A first MR signal corresponding to a first tissue and a second MR signal corresponding to a second tissue are identified. An RF pulse to be applied to the first and second tissues is selected. Based on at least the first MR signal, the second MR signal, and the RF pulse, an updated first MR signal and an updated second MR signal are determined. A difference is computed between the updated first MR signal and the updated second MR signal. The difference is added to an accumulated difference. The RF pulse selecting, updated first and second MR signal determination, difference computation and adding are repeated. The ANN is controlled to use reinforcement learning to select the MR imaging pulse sequence based, at least in part, on the accumulated difference.

17 Claims, 9 Drawing Sheets

MRI PULSE SEQUENCE DESIGN

FIELD

This disclosure relates generally to magnetic resonance (MR) imaging, and more specifically to MR pulse sequence design.

BACKGROUND

Due to the non-linearity of the MR imaging system, MR pulse sequence design has been a challenging task, relying on developers' experiences and involving laborious experimentation. Recently, a new technique MR Fingerprinting (MRF) has been proposed for MR quantitative imaging and shows promising advantages over conventional methods. The MRF sequence includes a long series of random flip angles (FA), acquisition period (AP), echo time, phase encoding, diffusion encoding, flow encoding and/or repetition times (TR). Alterations from a pure random sequence have been used and show varying performance.

SUMMARY

A method uses an artificial neural network (ANN) to automatically produce a magnetic resonance (MR) pulse sequence. A first MR signal corresponding to a first tissue and a second MR signal corresponding to a second tissue are identified. An RF pulse to be applied to the first tissue and the second tissue is selected. Based on at least the first MR signal, the second MR signal, and the RF pulse, an updated first MR signal and an updated second MR signal are determined. A difference is computed between the updated first MR signal and the updated second MR signal. The difference is added to an accumulated difference. The RF pulse selecting, updated first and second MR signal determination, difference computation and adding are repeated one or more times. The ANN is controlled to use reinforcement learning to select the MR imaging pulse sequence based, at least in part, on the accumulated difference.

In some embodiments, a method uses an artificial neural network (ANN) to automatically produce a magnetic resonance (MR) imaging pulse sequence. The data represent a first MR signal corresponding to a first tissue type and a second MR signal corresponding to a second tissue type. The data are converted into data representing a third signal and a fourth signal in a second signal space. The ANN is used to perform metric learning so as to learn the conversion from the first signal space to the second signal space, such that a distance between the third signal and the fourth signal in the second signal space is maximized. A pulse sequence is computed, such that when an MR scanner applies the pulse sequence to tissues of the first tissue type and the second tissue type, the third and fourth signals are generated in the second signal space.

In some embodiments, a method uses an artificial neural network (ANN) to automatically produce a magnetic resonance (MR) imaging pulse sequence and signal evolution. The data represent a first MR signal corresponding to a first tissue type and a second MR signal corresponding to a second tissue type. A reinforcement learning method is performed in the ANN to learn a signal evolution function to be applied by the ANN. The ANN is used to perform metric learning so as to learn a pulse sequence, such that when an MR scanner applies the pulse sequence to tissues of the first tissue type and the second tissue type, a first signal corresponding to the first tissue type and a second signal corresponding to the second tissue type are generated, and a difference between the first signal and the second signal is maximized.

DETAILED DESCRIPTION

This description of the exemplary embodiments is intended to be read in connection with the accompanying drawings, which are to be considered part of the entire written description.

System Architecture

Figure 1A:
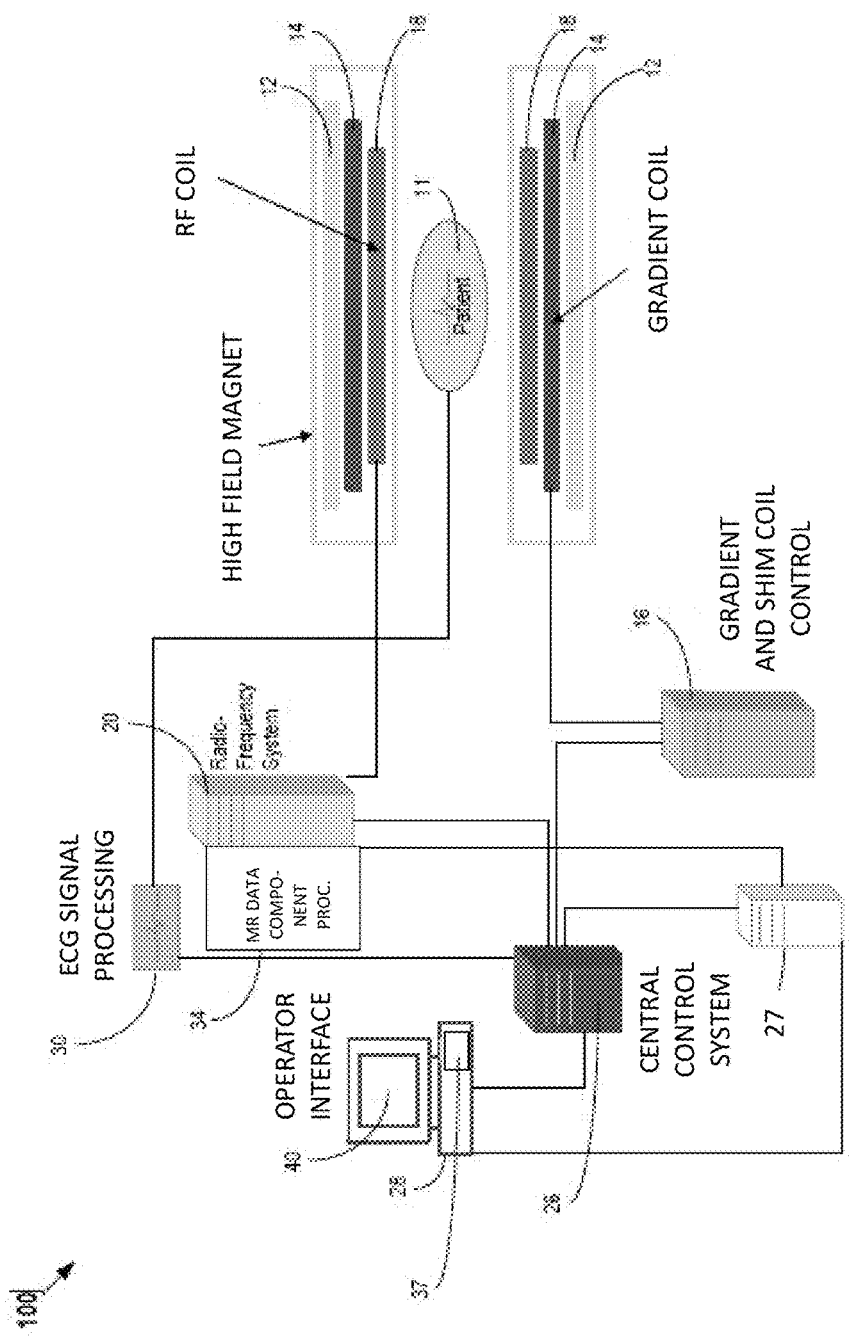
FIG. 1A is a block diagram of an embodiment of an MR system for medical imaging.

FIG. 1A shows an MR scanner system 100 for ordering acquisition of frequency domain components representing Magnetic Resonance (MR) image data for storage in an MR data storage array, as used by some embodiments. In MR scanner system 100, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences Ψ. The shimmed gradients compensate for inhomogeneity and variability in an MR imaging device magnetic field resulting from patient anatomical variation and other sources. The magnetic field gradients include a slice-selection gradient magnetic field, a phase-encoding gradient magnetic field and a readout gradient magnetic field that are applied to patient 11.

Further RF (radio frequency) module 20 provides RF pulse signals Ψ to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and MR data component processor unit 34 to provide an MR dataset to an image data processor for processing into an image. In some embodiments, the image data processor is located in central control unit 26. However, in other embodiments such as the one depicted in FIG. 1A, the image data processor is located in a separate unit 27. ECG synchronization signal generator 30 provides ECG signals used for pulse sequence and imaging synchronization. A two or three dimensional MR data storage array of individual data elements in MR data component processor unit 34 stores corresponding individual frequency components comprising an MR dataset. The MR data array of individual data elements has a designated center and individual data elements individually have a radius to the designated center.

A magnetic field generator (comprising coils 12, 14 and 18) generates a magnetic field for use in acquiring multiple individual frequency components corresponding to individual data elements in the storage array. The individual frequency components can be successively acquired using a Cartesian acquisition strategy, as the multiple individual frequency components are sequentially acquired during acquisition of an MR dataset representing an MR image. A storage processor in the MR data component processor unit 34 stores individual frequency components acquired using the magnetic field in corresponding individual data elements in the array. The row and/or column of corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components is substantially minimized.

Central control processor 26 is programmed to sample the MR signals according to a predetermined sampling pattern. Central control unit 26 also uses information stored in an internal database to process the detected MR signals in a coordinated manner to generate high quality images of a selected slice(s) of the body (e.g., using the image data processor) and adjusts other parameters of MR scanner system 100. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control unit 26 and enables user modification of magnetic resonance imaging signals in substantially real time. Display processor 37 processes the magnetic resonance signals to provide image representative data for display on display 40, for example.

MR scanner system 100 is only exemplary, and a variety of MR scanning systems can be used to collect the MR data.

In an MR scanning system 100, scanner parameters are selected to generate pulse sequences. Due to the uniqueness of the magnetic resonance fingerprinting (MRF) reconstruction and the enormous number of parameters available for tuning, additional sequence design methods are desired. Some examples of sequence generation methods include pseudo-random flip angles (FAs), acquisition periods (AP), and repetition times (TRs), perturbed sinusoidal wave, or random plus linear ramping. U.S. Patent Application Publication No. 2015/0302297 A1 describes a method for automatically generating a set of MR scanner parameters (e.g., FA and AP) that will result in a desired MR pulse sequence useful for MRF.

For MR imaging, one form of optimization is to achieve high contrast between regions representing different types of tissues in images reconstructed from sampled MR signals. The inventors have determined methods to automatically select scanner parameters to generate MR pulse sequences that optimize the contrast between tissues. The target setup parameters generate certain contrast between tissues. The system and method use an artificial neural network (ANN) to design a sequence to achieve optimized contrast. In some embodiments, the method generates the MR parameters without a priori knowledge of a specific signal evolution, based on a selection of two different tissue types. In some embodiments, the system uses an ANN to generate a sequence providing the desired contrast between the two tissue types.

Figure 1B:
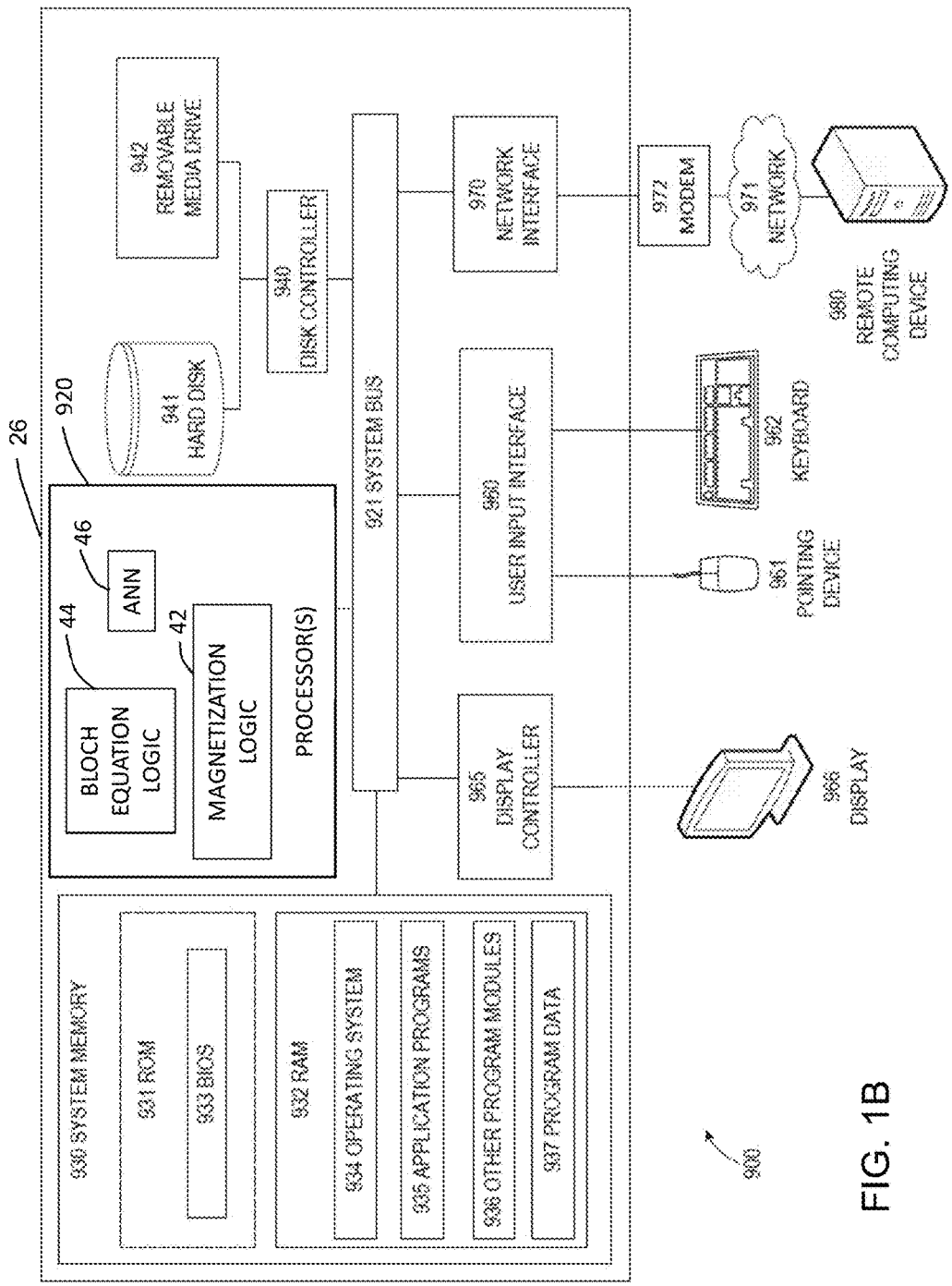
FIG. 1B is a detailed block diagram of an example of the computer system suitable for the system of FIG. 1A, according to some embodiments.

FIG. 1B illustrates an exemplary computing environment 900 within which includes an embodiments of the central control system 26 of FIG. 1A. For example, computing environment 900 can be used to implement one or more of the artificial neural networks described below. Computers and computing environments, such as central control system 26 and computing environment 900, are known to those of skill in the art and thus are described briefly here.

As shown in FIG. 1B, the central control system 26 can include a communication mechanism such as a system bus 921 or other communication mechanism for communicating information within the central control system 26. The central control system 26 further includes one or more processors 920 coupled with the system bus 921 for processing the information.

The processors 920 include magnetization logic 42 that provides initial magnetization values to the ANN block 46. The initial magnetization values may be randomly selected. The Bloch equation logic 44 produces the in-process magnetization values based, at least in part, on the selected pulse sequence parameter. For example, the selected pulse sequence parameter may be used as one of the values in a Bloch equation. The selected pulse sequence parameter may be used to update the ANN block 46. The ANN block 46 may be updated using unsupervised learning. Although FIG. 1B shows magnetization logic 42, Bloch equation logic 44, and ANN block 46 as separate blocks, these components can be hosted by one processor, or by two or three different processors.

In some embodiments, ANN block 46 is deep neural network (DNN) having multiple hidden layers of units (not shown) between the input and output layers. A DNN can generate compositional models for expressing the system as a layered composition. The upper layers compose features from the lower layers. In some embodiments, the ANN block 46 is a DNN designed as a feedforward network.

The processors 920 can include one or more central processing units (CPUs), graphical processing units (CPUs), or other suitable processor. More generally, a processor can include a device for executing machine-readable instructions stored on a computer readable medium, for performing tasks and can comprise any one or combination of, hardware and firmware. A processor can also comprise memory storing machine-readable instructions executable for performing tasks. A processor acts upon information by manipulating, analyzing, modifying, converting or transmitting information for use by an executable procedure or an information device, and/or by routing the information to an output device. A processor can use or comprise the capabilities of a computer, controller or microprocessor, for example, and be conditioned using executable instructions to perform special purpose functions not performed by a general purpose computer. A processor can be coupled (electrically and/or as comprising executable components) with any other processor enabling interaction and/or communication therebetween. A user interface processor or generator can include electronic circuitry or software or a combination of both for generating display images or portions thereof. A user interface can comprise one or more display images enabling user interaction with a processor or other device.

Continuing with reference to FIG. 1B, the central control system 26 also includes a system memory 930 coupled to the system bus 921 for storing information and instructions to be executed by processors 920. The system memory 930 can include computer readable storage media in the form of volatile and/or nonvolatile memory, such as read only memory (ROM) 931 and/or random access memory (RAM) 932. The RAM 932 can include other dynamic storage device(s) (e.g., dynamic RAM, static RAM, and synchronous DRAM). The ROM 931 can include other static storage device(s) (e.g., programmable ROM, erasable PROM, and electrically erasable PROM). In addition, the system memory 930 can be used for storing temporary variables or other intermediate information during the execution of instructions by the processors 920. A basic input/output system 933 (BIOS) containing the basic routines that help to transfer information between elements within central control system 26, such as during start-up, can be stored in the ROM 931. RAM 932 can contain data and/or program modules that are immediately accessible to and/or presently being operated on by the processors 920. System memory 930 can additionally include, for example, operating system 934, application programs 935, other program modules 936 and program data 937.

The central control system 26 can also include a disk controller 940 coupled to the system bus 921 to control one or more storage devices for storing information and instructions, such as a magnetic hard disk 941 and a removable media drive 942 (e.g., floppy disk drive, compact disc drive, tape drive, and/or solid state drive). Storage devices can be added to the central control system 26 using an appropriate device interface (e.g., a small computer system interface (SCSI), integrated device electronics (IDE), Universal Serial Bus (USB), or FireWire).

The central control system 26 can also include a display controller 965 coupled to the system bus 921 to control a display or monitor 966, such as a liquid crystal display (LCD), for displaying information to a computer user. The computer system includes an input interface 960 and one or more input devices, such as a keyboard 962 and a pointing device 961, for interacting with a computer user and providing information to the processors 920. The pointing device 961, for example, can be a mouse, a light pen, a trackball, or a joy stick for communicating direction information and command selections to the processors 920 and for controlling cursor movement on the display 966. The display 966 can provide a touch screen interface which allows input to supplement or replace the communication of direction information and command selections by the pointing device 961.

The central control system 26 can perform a portion or all of the processing steps of embodiments in response to the processors 920 executing one or more sequences of one or more instructions contained in a memory, such as the system memory 930. Such instructions can be read into the system memory 930 from another computer readable medium, such as a magnetic hard disk 941 or a removable media drive 942. The magnetic hard disk 941 can contain one or more data stores and data files used by various embodiments. Data store contents and data files can be encrypted to improve security. The processors 920 can also be employed in a multi-processing arrangement to execute the one or more sequences of instructions contained in system memory 930. In alternative embodiments, hard-wired circuitry can be used in place of or in combination with software instructions. Thus, embodiments are not limited to any specific combination of hardware circuitry and software.

Some embodiments include software instructions written in a high level language, such as C, C++, C#, Java, Fortran or Python. Some embodiments are written for a multi-paradigm numerical computing environment, such as Matlab, sold by Mathworks, Inc. of Natick, Mass., or the like.

As stated above, the central control system 26 can include at least one computer readable medium or memory for holding instructions and for containing data structures, tables, records, or other data described herein. The term "computer readable medium" as used herein refers to any non-transitory machine-readable storage medium that stores instructions or data and may be accessed for reading and/or writing by the processors 920. A computer readable medium can take many forms including, but not limited to, non-transitory, non-volatile media and volatile media. Non-limiting examples of non-volatile media include optical disks, solid state drives, magnetic disks, and magneto-optical disks, such as magnetic hard disk 941 or removable media drive 942. Non-limiting examples of volatile media include dynamic memory, such as dynamic random access memory 930.

The central control system 26 can operate in a networked environment using logical connections to one or more remote computers, such as remote computing device 980. Remote computing device 980 can be a personal computer (laptop or desktop), a mobile device, a server, a router, a network PC, a peer device or other common network node, and typically includes many or all of the elements described above relative to central control system 26. When used in a networking environment, central control system 26 can include modem 972 for establishing communications over a network 971, such as the Internet. Modem 972 can be connected to system bus 921 via user network interface 970, or via another appropriate mechanism.

Network 971 can include, but is not limited to, the Internet, an intranet, a local area network (LAN), a wide area network (WAN), a metropolitan area network (MAN), a personal area network (PAN) a direct connection or series of connections, a cellular telephone network, or any other network or medium capable of facilitating communication between central control system 26 and other computers (e.g., remote computing device 980). The network 971 can be wired, wireless or a combination thereof. Wired connections can be implemented using Ethernet, Universal Serial Bus (USB), RJ-6, or any other wired connection. Wireless connections can be implemented using Wi-Fi, WiMAX, and Bluetooth, infrared, cellular networks, satellite or any other wireless connection methodology. Additionally, several networks can work alone or in communication with each other to facilitate communication in the network 971.

Aside from the computing environment 900 shown in FIG. 1B, the methods and systems described herein can be implemented in specialized computing environments. For example, in some embodiments, a plurality of processors can be configured to parallelize at least one of the decomposition operations, the non-linear thresholding, and/or the reconstruction operations performed by the neural networks described above. These processors can be arranged, for example, in a parallel computing platform using technologies such as "Apache Spark™"or "NVIDIA CUDA™".

The functions and process steps described herein can be performed automatically or wholly or partially in response to user command. An activity (including a step) performed automatically is performed in response to one or more executable instructions or device operation without user direct initiation of the activity.

Methods described herein use learning-based techniques for MR and MRF sequence design. Three distinct strategies are described below, including reinforcement learning, metric learning, and a comprehensive learning model. An MRF sequence design is described in detail. But the methods are not limited to MRF and can also be applied to MR imaging sequence design generation.

The methods described below can use unsupervised learning to determine signal evolution produced by RF pulse sequences for maximizing MR image contrast, and/or optimal pulse sequences for maximizing image contrast. The methods do not require a priori knowledge of the signal evolution from an RF pulse or of the signal sequence that optimizes MR image contrast.

The pulse sequence can vary a variety of parameters such as echo time, flip angle (FA), phase encoding, diffusion encoding, flow encoding, RF pulse amplitude, RF pulse phase, number of RF pulses, number and/or type of gradient applied between an excitation portion of a sequence block and a readout portion of a sequence block, number and/or type of gradient applied between a readout portion of a sequence block and an excitation portion of a sequence block, number and/or type of gradient applied during a readout portion of a sequence block, amount of RF spoiling, or amount of gradient spoiling between sequence blocks.

I. Reinforcement Learning

The signal evolution of MR can be described as:

$$M_i = Q_i E_i M_{i-1}, \quad (1)$$

where $M_i$ is the magnetization vector at the $i^{th}$ TR. $E_i$ represents the relaxation effect and is a function of tissue specific parameters such as T1 (rate of longitudinal relaxation) and T2 (rate of transverse relaxation). $Q_i$ represents the rotation effect which is related to sequence design, such as the FA at the $i^{th}$ TR. The in-plane components of $M_i$ contribute to the signal at the $i^{th}$ TR, $S_i$. In some embodiments, the method formulates the object of a sequence design to maximize the image contrast, that is, the differences between the signals from different tissues S and S'. In other embodiments, the method formulates the sequence to achieve a desired level of contrast in the minimum amount of time.

A reinforcement learning method is concerned with how a software agent should take action in an environment described as a Markov Decision Process (MDP) so as to maximize a total reward. In an MDP, outcomes are partly random (determined by the environment) and partly under the control of an agent responding to the environment. In an MDP, the actions available to the agent when in a given state are dependent on that state. At each point in time t, the agent performs an action $a_t$ and the environment generates an observation $o_t$ resulting in an instantaneous reward $R_t$. A policy defines a respective probability distribution of actions the agent may perform for each respective state.

Using an MDP model in this method, reinforcement learning identifies a policy for selecting actions (RF pulses) that maximizes the long-term reward, i.e., the expected accumulated reward (accumulated difference between signals output by two different tissue types). Using this strategy, there is no need to know the pulse sequence of signal evolution in advance, Beginning with an initial magnetization state $M_i$, the system learns a sequence of pulses and a corresponding sequence of signals based on the end target of maximizing contrast.

At each time, the agent makes an observation, which results in a reward. An action is then selected from a set of actions. The action causes the environment to transition to a new state, and the reward associated with that transition is determined. The sequence of actions is optimized to maximize the total reward from the sequence over time. Reinforcement learning includes learning a policy function that estimates the total future rewards that can be achieved from any given state, so that the agent can decide the next action based not only on its immediate reward, but also on the long-term future.

For applying reinforcement learning to the sequence generation problem, the state is the Magnetization $M_i$ (spin-state), the action is an RF pulse, the observation is the signal, and the reward at each time step is the difference between the respective signals corresponding to the tissue type S and the tissue type S'.

Figure 2:
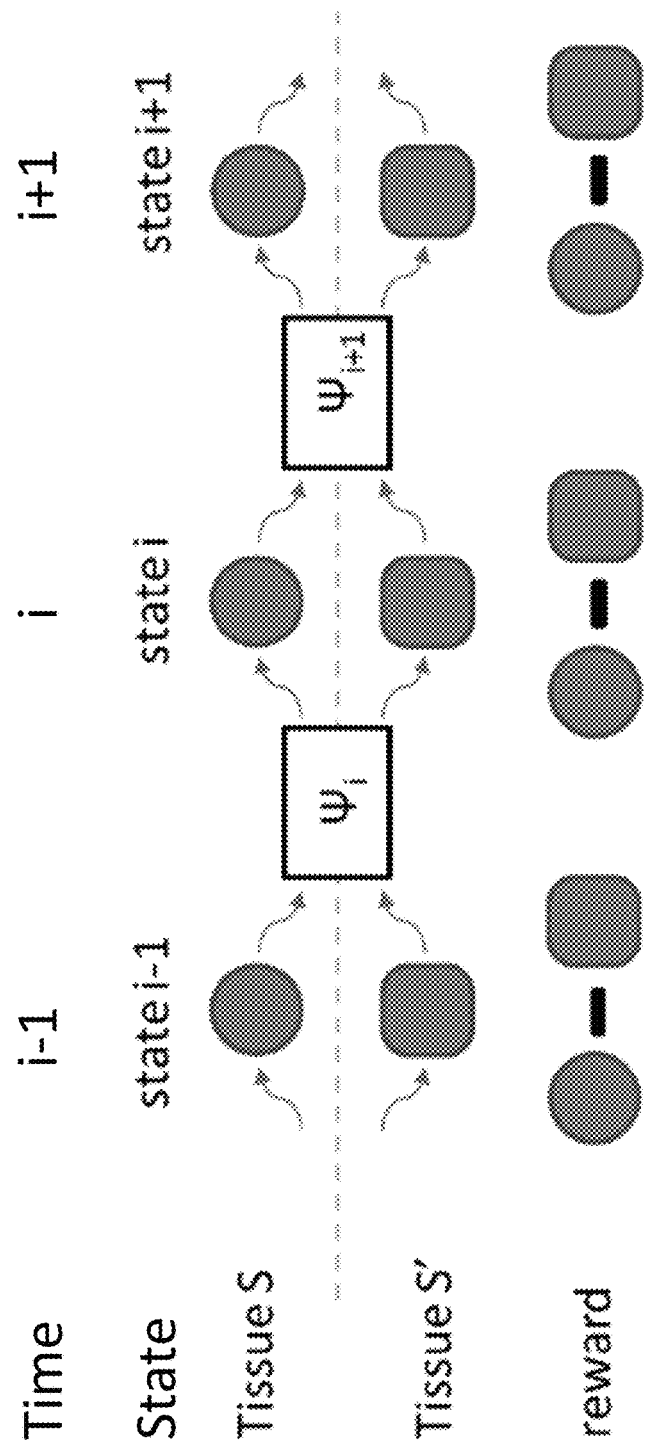
FIG. 2 is a schematic diagram of a reinforcement learning method for learning an pulse sequence.

FIG. 2 shows the MDP model for the sequence design. Using the MDP model, at each time step i, the tissue has a magnetization state $M_i$ corresponding to a signal $s_i$, and the system may choose any pulse sequence $\Psi$ that is available while the spin state corresponds to the signal $s_i$. The magnetization state $M_{i+1}$ at the next time step i+1 is assumed to randomly change into a new state corresponding to a signal $s_{i+1}$, and provide a corresponding reward $R(s, s_{i+1})$. The probability that the magnetization state $M_i$ changes into its new state $M_{i+1}$ and results in the signal $s_{i+1}$ is influenced by the chosen sequence $\Psi$, and is given by the state transition function $F(s, s_{i+1})$. Thus, the next magnetization state $M_{i+1}$ corresponding to the signal $s_{i+1}$ depends on the current magnetization state $M_i$ (corresponding to signal s) and the sequence $\Psi$.

In some embodiments, the design of an MR pulse sequence is solved by reinforcement learning. The signal evolution of MR and the target of the sequence design, as described above, follow a reinforcement learning scheme. Magnetization $M_i$ for a range of tissues at the $i^{th}$ TR is considered as the state at time i, and the effect of rotation and relaxation is considered as the "action $\Psi$" to transition $M_i$ from one state to another. At each state, the set of available transitions depends on the current state. The "reward" is the difference in the resulting signals in each respective tissue S, S' and so on, of different tissue parameters, i.e. the system learns to maximize the contrast between different tissues. The goal is to maximize this reward over the whole sequence (as illustrated in FIG. 2).

FIG. 2 shows the process flow for two different types of tissues, S and S' (e.g., muscle and fat) during the course of scanning. The states of tissue S are indicated by circles, and the states of tissue S' are indicated by squares. Each tissue has different density, resonant frequency, T1 (rate of longitudinal relaxation) and/or T2 (rate of transverse relaxation). The MR scanner system 100 uses a sequence of radio frequency (RF) pulses $\Psi_i$ to generate signals. The MR scanner system 100 applies certain amounts of energy to generate signals in the patient's body. When both tissues S and S' are subjected to the same RF pulse, they respond differently to the excitation.

If a tissue has a state 1 and the MR scanner system 100 applies an RF pulse at time t1, the spin state changes from state 1 to state 2, causing the tissue to generate different signals.

In the example of FIG. 2, at time i−1, each tissue S, S' has a respective magnetization spin state$_{i-1}$ indicated by the circle and square symbols. The reward is indicated by the difference between the two states, where a larger difference is correlated with a greater contrast between tissues S and S'.

The tissues S and S' undergo an RF pulse $\Psi_i$ causing rotations and relaxations resulting in each tissue type S and S' transitioning to a respective magnetization spin state$_i$. The reward at time i is again determined by the difference between the magnetization states of the tissues S and S'.

In response to the pulse $\Psi_{i+1}$ the tissues S and S' undergo another set of rotations and relaxations resulting in each tissue type transitioning to a respective magnetization spin state$_{i+1}$. The reward at time i+1 is again determined by the difference between the magnetization states of the tissues S and S'. Each time a same or a different RF pulse is applied, the spin states vary accordingly, generating a time series of signals, and a reward is added to the accumulated reward.

The accumulated reward (difference between the states of the two tissues S and S') is computed over all or a subset of the states. Because it is desirable to maximize the contrast, it is desirable to use the pulse sequence that maximizes the accumulated reward.

In some embodiments, Monte Carlo methods are used to evaluate the RF pulse distribution for each respective spin-state $M_i$. Given an RF pulse distribution function for each spin-state $M_i$, the reward for each spin-state/RF pulse pair ("state-pulse pair") are computed for all state-pulse pairs. A table representing the expected reward of applying a given pulse when in a given spin-state can be stored in the memory. The estimate of the reward for a given state-pulse pair can be computed by averaging the sampled returns which originated from that state-pulse pair over many Monte Carlo trials. The method can generate an estimate of the reward function for every state-pulse pair.

In some embodiments, having generated the estimate of the reward function for every state-pulse pair, an optimal RF pulse (having the largest expected reward) is determined for each respective state, by summing the rewards for the state over all of its pulse values.

In other embodiments, the RF pulse distribution is evaluated by a temporal difference method, a policy gradient method, simulated annealing, a cross-entropy search, an evolutionary computation method or the like.

In reinforcement learning, the system solves the states time point by time point, accumulating the reward with every step. In some embodiments, the application of reinforcement learning to sequence generation is considered a non-episodic problem, i.e., there is no predetermined terminal state to be reached. In the non-episodic case, the reward can be discounted. Discounting makes the initial time steps more important, and reduces the reward received after many steps.

In some embodiments, the accumulated reward is given by:

$$R=\Sigma_{t=0}^{\infty}\gamma^t r_{t+1} \quad (2)$$

Here R is the total accumulated reward (also called the return), $\gamma$ is a discount factor between 0 and 1, and r is the reward received after the $t^{th}$ transition. The closer $\gamma$ is to zero, the greater the return for shorter pulse sequences with high contrast. The closer $\gamma$ is to one, the greater the return for pulse sequences that maximize contrast (i.e., maximizes the difference between signals for the two tissues S and S') regardless of sequence length.

Using the proposed reinforcement learning strategy, the sequence design can be set to maximize the contrast in the images, as discussed above.

In other embodiments, the accumulated reward (difference between signals) can be defined using various types of metrics, including but not limited to the l1 norm (Manhattan distance), the l2 norm (Euclidean distance), or a learned metric.

Alternatively, using the reinforcement learning strategy, the sequence design can also be set to minimize the sequence length given a desired image contrast level.

In some embodiments, to acquire an image, a single pulse may be insufficient time to sample enough measurements, so it is desirable to generate multiple RF pulses which generate the same contrast. Then pulses are generated at multiple time points to result in the same contrast. Each state corresponds to one instance where measurements are taken, and each action corresponds to a respective pulse (which can be different from each other). The system uses the ANN to learn the pulses to apply at each time point that will result in the same contrast to achieve consistent contrast.

Figure 3:
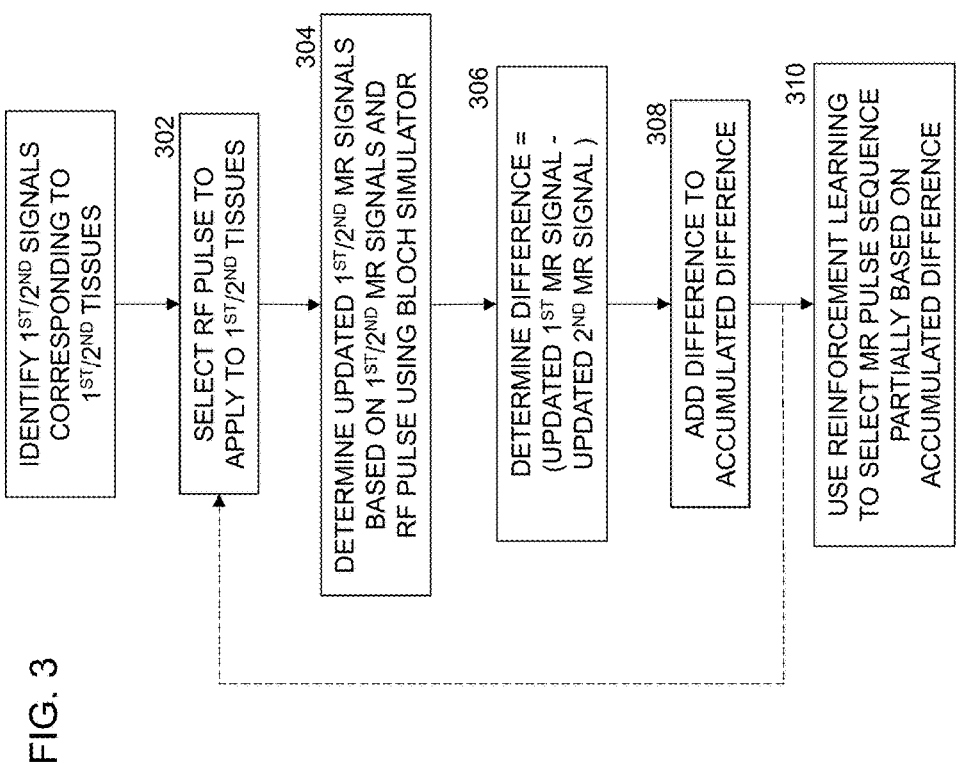
FIG. 3 is a flow chart of an exemplary reinforcement learning method according to FIG. 2.

FIG. 3 is a flow chart of an exemplary method for using an artificial neural network (ANN) to automatically produce a magnetic resonance (MR) imaging pulse sequence using reinforcement learning.

At step 300, a first MR signal corresponding to a first tissue and a second MR signal corresponding to a second tissue are identified.

At step 302, an RF pulse is selected to be applied to the first tissue and the second tissue.

At step 304, based on at least the first MR signal, the second MR signal, and the RF pulse an updated first MR signal and an updated second MR signal are determined. In some embodiments, a Bloch simulator computes the updated first MR signal and the updated second MR signal. For example, the simulator can compute the updated first MR signal and the updated second MR signal based on a rate of longitudinal relaxation (T1) of the first tissue or the second tissue that changes over time or a rate of transverse relaxation (T2) of the first tissue or the second tissue that varies over time.

In other embodiments, the RF pulse is applied to the first tissue and the second tissue, and the updated first MR signal and the updated second MR signal are measured using the MRI scanner system 100.

At step 306, a reward is computed. For example, the reward can be a difference between the updated first MR signal and the updated second MR signal.

At step 308, the reward (e.g., the difference) is added to an accumulated difference.

Steps 302 to 308 are repeated one or more times for different RF pulses.

At step 310, the ANN is controlled to use reinforcement learning to select the MR imaging pulse sequence based, at least in part, on the accumulated difference.

Figure 4:
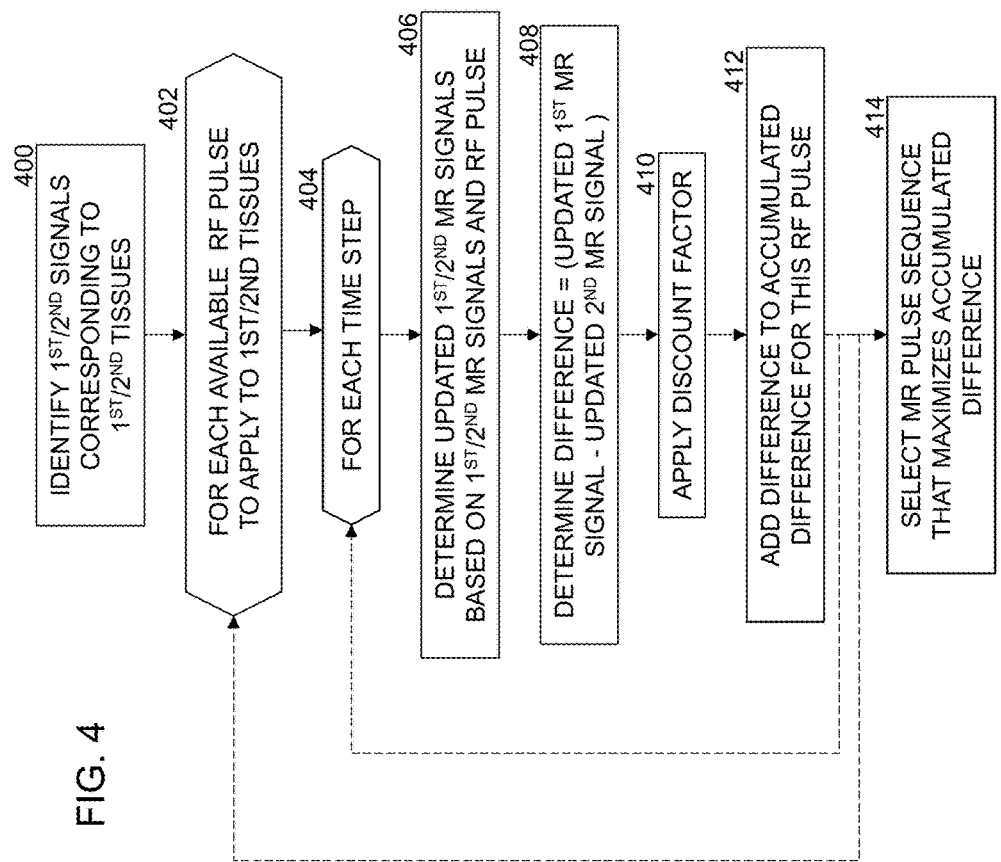
FIG. 4 is a detailed embodiment of a reinforcement learning method.

FIG. 4 is a flow chart of an implementation of the method of FIG. 3 for using an ANN to automatically produce an MR imaging pulse sequence using reinforcement learning.

At step 400, a first MR signal corresponding to a first tissue and a second MR signal corresponding to a second tissue are identified.

At step 402, a loop including steps 404 to 412 is repeated for each available RF pulse that the MR scanner is capable of applying. This loop determines an accumulated (total) reward for each available RF pulse.

At step 404, a loop including steps 406 to 412 is repeated for each time step. This loop determines the accumulated (total) reward for one RF pulse over time.

At step 406, based on at least the first MR signal, the second MR signal, and the RF pulse, an updated first MR signal and an updated second MR signal are determined. In some embodiments, a Bloch simulator computes the updated first MR signal and the updated second MR signal. In other embodiments, the RF pulse is applied to the first tissue and the second tissue, and the updated first MR signal and the updated second MR signal are measured using the MRI scanner system 100.

At step 408, a reward is calculated. For example, the reward can be a difference between the updated first MR signal and the updated second MR signal is computed.

At step 410, a discount factor corresponding to the current time step is computed, and applied by multiplying the discount factor and the reward for the current time. For example the discount factor can be calculated using equation (2).

At step 412, the discounted difference is added to the accumulated difference corresponding to the RF pulse.

At step 414, the MR pulse sequence that maximizes the accumulated difference is selected. In some embodiments, the MR imaging pulse sequence is selected so as to maximize the accumulated difference given a fixed length of the MR imaging pulse sequence. In other embodiments, the MR imaging pulse sequence is selected so as to minimize a length of the MR imaging pulse sequence given a fixed value of the accumulated difference (i.e., the shortest sequence to yield a desired contrast).

Using the proposed reinforcement learning strategy, the sequence design can also be formed to achieve a desired signal evolution for a certain tissue. In this case, the entire first signal X (corresponding to the first tissue type S) is given and the sequence Ψ is learned to generate a second signal X' (corresponding to the same tissue type S) that minimize the distance between X and X'. A possible application is MR fingerprinting.

The signal X can be further modeled to include physiological effects such as partial volume, perfusion, diffusion and etc. In some embodiments, the updated first MR signal and the updated second MR signal are further based on at least one of the group consisting of a partial volume parameter, a perfusion parameter, and a diffusion parameter.

The pulse sequence design task under the above method can be application-oriented. The image contrast to be maximized can be selected in a specific application according to scanning needs. Examples include to maximize pathology contrast, to maximize grey and white matter contrast, to maximize contrast enhanced and unenhanced contrast and etc.

In some embodiments, the pulse sequence is designed for MR imaging with three types of tissue present. If an MR image contains more than two tissue types, there is tradeoff. Increasing the difference between the first and second types of tissues can reduce the difference between the second and third types of tissues. If optimizing the difference between the first and second tissues, for more than two types of tissues, different weights can be applied to each tissue type in the signal evolution model to identify which tissues are more important to distinguish from each other. The system can maximize the weighted sum of pairwise differences for the two tissue types of greatest interest.

The Signal X can be further modeled to include physical effects (e.g., partial volume, perfusion, diffusion resonant frequency, diffusion co-efficient, spin density, proton density). This can be accomplished using a more complex signal generating model. For example, in addition to the parameters T1, T2, a perfusion parameter can be added to the model based on Bloch-McConnell equations.

The above system and method solves the problem of optimizing pulse sequence as a reinforcement learning problem. It can be applied to multiple types of sequences such as, but not limited to, fast low angle shot (FLASH), turbo gradient spin echo (TGSE), fast imaging with steady-state precession (FISP), balanced sequence true FISP (TrueFISP) and MR fingerprinting.

II. Metric Learning

The metric learning strategy (also known as manifold learning) formulates the object of a pulse sequence (Ψ) design to maximize image contrast, i.e., the differences between the signals from different tissues S and S'.

The object of maximizing image contrasts can be achieved by metric learning. A network learns to convert the signals to a second space (manifold) in which the inter-class distance is maximized and intra-class distance is minimized. This task can be approached as a clustering problem. The method can use metric learning to do clustering. A clustering method (e.g., a K-means algorithm) is used, and the ANN can be used to machine-learn a distance metric that maximizes inter-class distance and minimizes intra-class distance. In this case, each of the classes can correspond to a respectively different tissue type. For example, the ANN may use the l1 norm (the Manhattan distance), the l2 norm (the Euclidean distance), or another distance metric that applies different weights to signals acquired at respectively different points in time to maximize inter-class distance and minimize intra-class distance.

Figure 5:
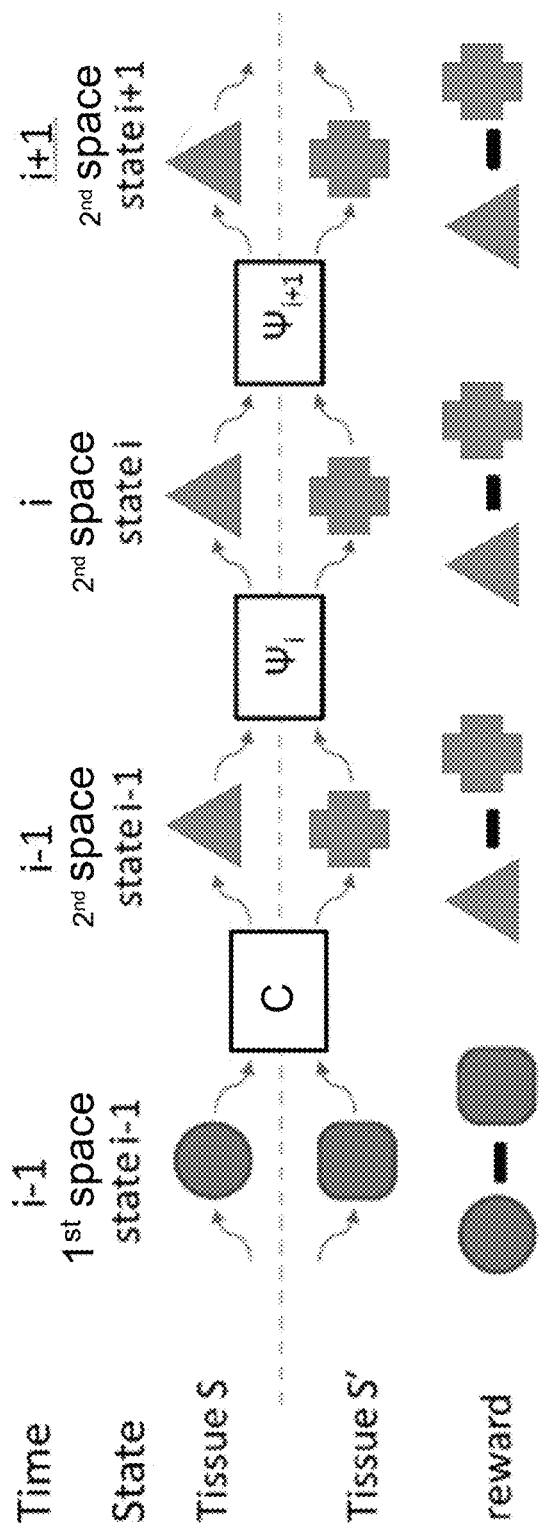
FIG. 5 is a schematic diagram of a metric learning method for learning a transformation between a first space and a second space.

FIG. 5 is a schematic diagram showing a metric learning strategy, using the format of FIG. 2. At time i−1, the state of the system is the same as discussed above with respect to the corresponding time step in FIG. 2. The circle and square represent the magnetization state $M_{i-1}$ of the first tissue S and the second tissue S' in a first space.

The state data at time i−1 are converted by a transformation C from a first space to a second space. The second space can represent a principal coordinate system of the magnetization state data, and can reduce the dimensionality of the tissue parameters. The transformation C is determined by machine learning, and need not be known in advance. The state data in the second space is represented in FIG. 5 by triangles and crosses.

In some embodiments, once the magnetization state data are converted from the first space to the second space, the pulse sequence Ψ can be determined by machine learning (similar to the reinforcement learning method described above with respect to FIGS. 2-4. In other embodiments, after the conversion, the pulse sequence is determined by another method.

Figure 6:
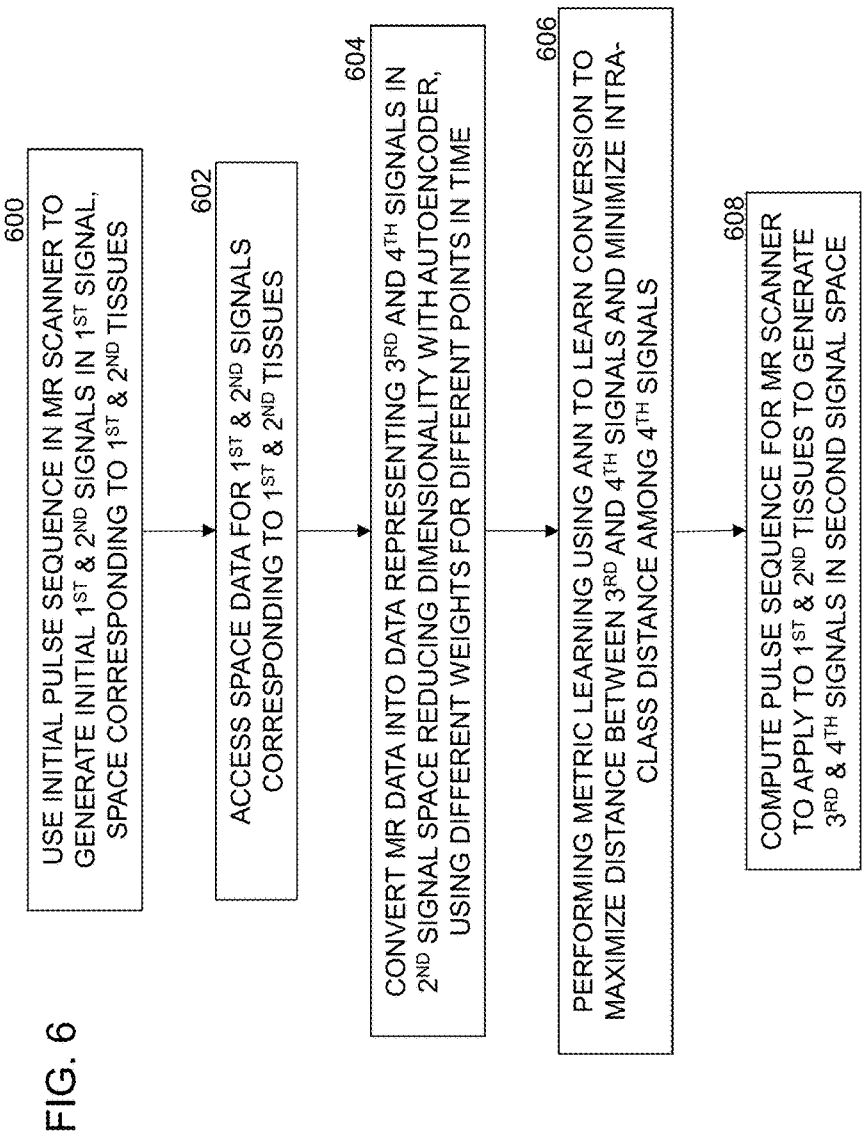
FIG. 6 is a is a flow chart of an exemplary metric learning method according to FIG. 5.

FIG. 6 is a flow chart of an exemplary metric learning method as shown schematically in FIG. 5.

At step 600, an initial pulse sequence is used in the MR scanner system 100 to generate an initial first MR signal corresponding to a first tissue S and an initial $2^{nd}$ MR signal corresponding to a second tissue S'.

At step 602, MR data representing the first MR signal corresponding to a first tissue type S and a second MR signal corresponding to a second tissue type S' are accessed.

At step 604, the MR data are converted into data representing a third signal and a fourth signal in a second signal space. In some embodiments, the conversion is selected to minimize intra-class distance among third signals corresponding to the first tissue type and minimize intra-class distance among fourth signals corresponding to the second tissue type. The conversion can include dimensionality reduction. Step 604 can be performed by an autoencoder, for example. The second signal space can be a principal coordinate system. In some embodiments, the MR data correspond to two or more different points in time, and the conversion includes applying respectively different weights to MR data from different points in time.

The learned conversion is subjected to physical constraints, so the generated pulse sequence and the resulting MR signals in the second space can be realized in an MR scanner.

At step 606, the ANN performs metric learning so as to learn a conversion from the first signal space to the second signal space to be used in step 604, such that a distance between the third signal and the fourth signal in the second signal space is maximized. The ANN learns the conversion, so the converted signal can still be realized by a pulse sequence that can be supplied to the MR scanner, such that, when the pulse sequence is applied to the coils of the MR scanner, the MR scanner will generate the signals in the second signal space. In the second signal space, the distance between the two is maximized.

At 608, a pulse sequence is computed, such that when an MR scanner applies the pulse sequence to tissues of the first tissue type and the second tissue type, the third and fourth signals are generated in the second signal space. In some embodiments, step 608 uses machine learning to compute the pulse sequence. The pulse sequence computed in step 608 is different from the initial pulse sequence.

The pulse sequence ($\Psi_i$) is computed to realize the converted signals such that, when the pulse sequence is used for MR imaging of the two types of tissue, the signals are generated in the second space (manifold) where the distance between the signals is maximized, thereby maximizing contrast. In some embodiments, the pulse sequence is also learned by machine learning. In other embodiments, the pulse sequence is computed by a non-learning method.

The original signals X and X' from different tissues generated by any sequence are classified as different classes. The method uses machine-learning to determine how to convert the signals X and X' to signals Y and Y' in a second space (manifold), where the distance between Y and Y' is maximized. The conversion is bounded by physical constraints such that the converted signals are realizable.

Using the proposed metric learning strategy, the sequence design goal can be set to maximize the contrast in the images.

For example, a metric learning method can apply different weights on respectively different time points. Consider a sequence that generates different signals for S and S'. The ANN can machine-learn a conversion to convert an MR signal to a second space (manifold), so the contrast between the two tissue types is maximized in the second space. The ANN then uses the converted signals to generate a pulse sequence, which can produce the desired signals in the second space.

The metric learning strategy can be used to image the subject as a static problem, without dynamic modelling. The two tissue types are considered using a physical model that defines allowable sequences.

In some embodiments, the conversion is an autoencoder, which maintains the length of the original sequence. This allows machine-learning of the pulse sequence having the maximum contrast among all pulse sequences having the same length as the original sequence. The autoencoder performs dimensionality reduction, reducing the number of random variables under consideration by obtaining a set of principal variables.

The conversion can also decrease the length of the sequence, where the length of Y is smaller than that of X. For example, a metric learning method can apply different weights on respectively different time points, such that the ANN can machine-learn a conversion to convert an MR signal to a second space, in which the distance between the signals is fixed in the second space, and the length of the sequence is minimized. The ANN then uses the converted signals to generate a pulse sequence, which can produce the desired signals in the second space.

The signal X can be further modeled to include physiological effects such as partial volume, perfusion, diffusion and etc.

The difference between signals can be defined using various types of metrics, including but not limited to l1, l2 and etc.

The sequence design task under the proposed invention scheme can be application oriented. The image contrast to be maximized can be selected in specific application according to scanning needs. Examples include to maximize pathology contrast, to maximize grey and white matter contrast, to maximize contrast enhanced and unenhanced contrast and etc.

III. Comprehensive Learning Model

Figure 7:
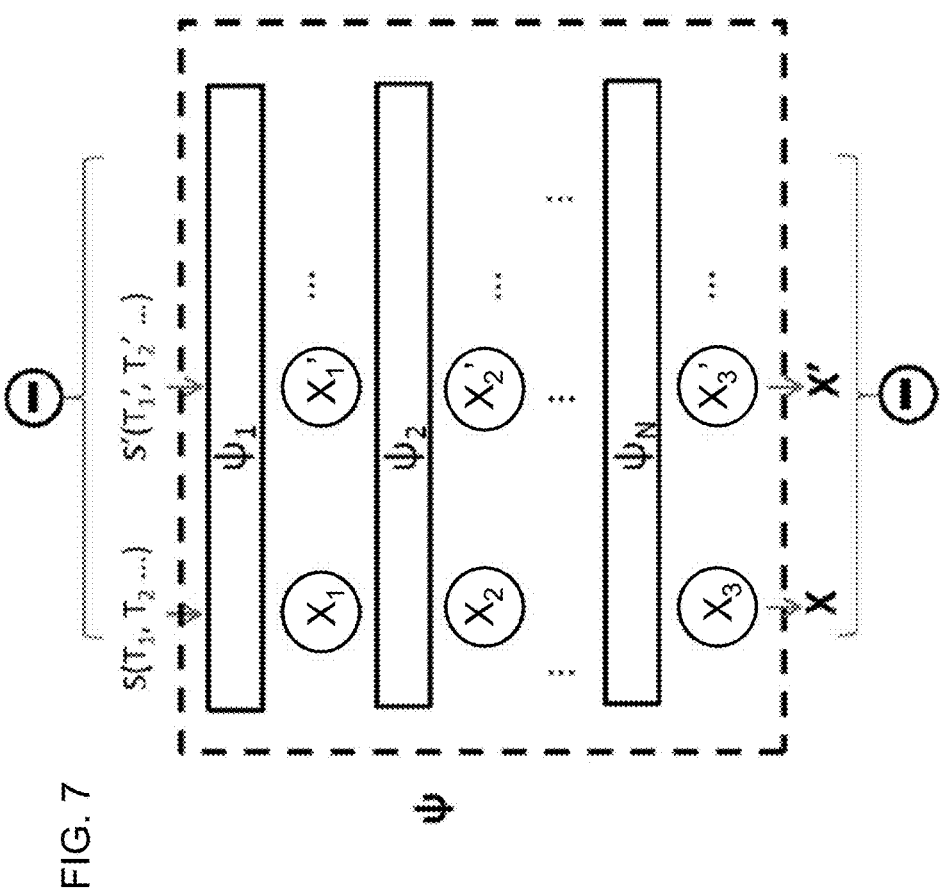
FIG. 7 is a schematic diagram of a comprehensive learning method for learning a signal evolution and a transformation between a first space and a second space.

FIG. 7 is a schematic diagram of a comprehensive learning model for an ANN. The comprehensive learning model is based on a combination of the reinforcement learning and metric learning strategies described above.

The signal evolution is modeled as in the reinforcement learning method of FIG. 2. That is, the ANN includes a signal evolution model, and the ANN uses reinforcement learning to learn the signal evolution while also using metric learning to learn the pulse sequence $\Psi_i$ as described above. Because the signal evolution and the pulse sequence are both learned, the comprehensive learning method does not need to apply the physical constraints that are included in the metric learning method described above. The ANN optimizes the signal evolution, inherently learning a ($\Psi_i$) that satisfies physical constraints.

As different tissues S and S' are fed into the network, the MR signal evolves through a sequence $\Psi$ of pulses, and the ANN outputs the signal X and X'. The goal is to maximize the distance between X and X' while S and S' are far apart in the corresponding tissue parameter space. The ANN performs a metric learning process using explicitly defined MR pulse sequences ($\Psi_i$), i.e., the MR pulse sequences are modeled inside the ANN and are explicitly learned using the ANN while the conversion is learned. Thus the MR pulse sequence $\Psi$ can be directly learned through the metric learning process (shown in FIG. 7).

Figure 8:
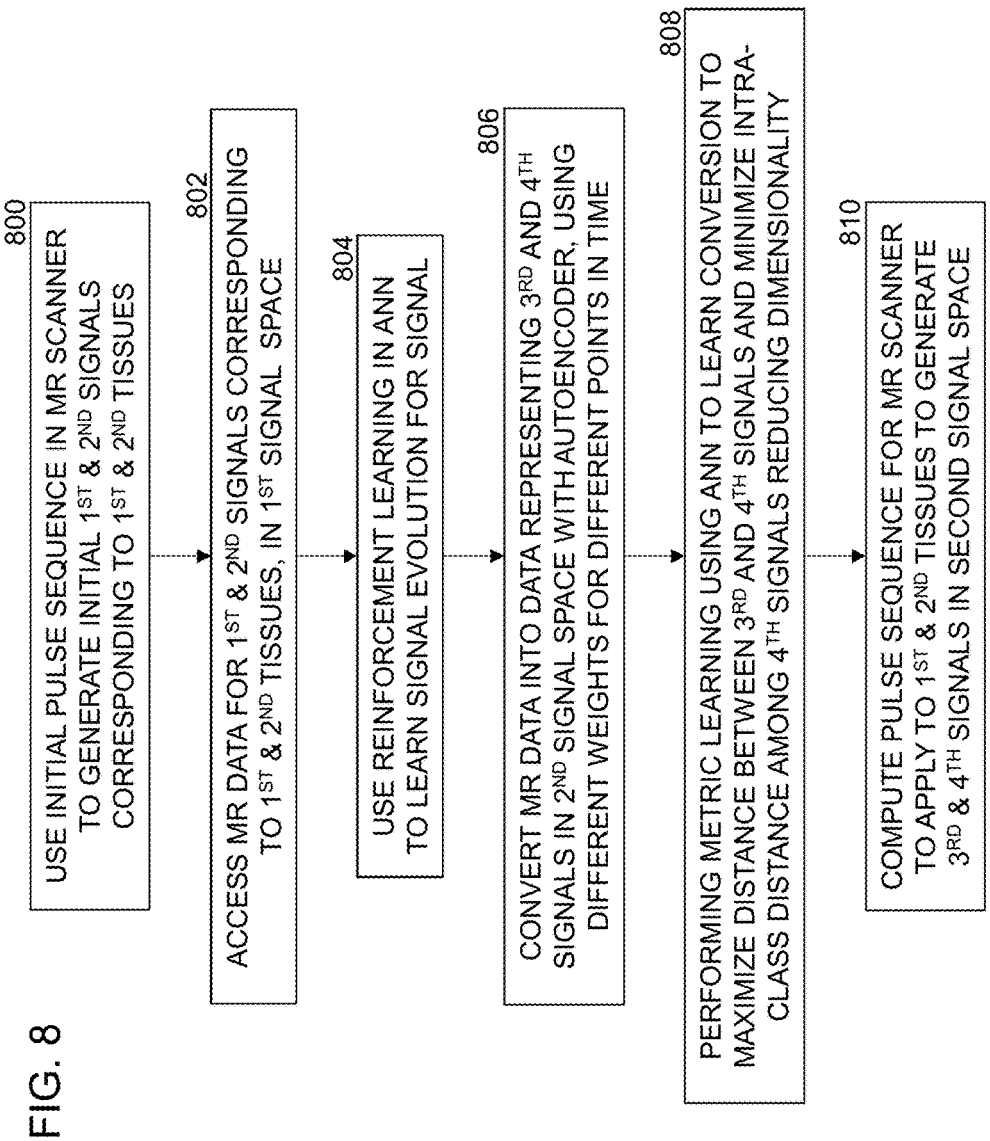
FIG. 8 is a is a flow chart of an exemplary comprehensive learning method according to FIG. 7.

FIG. 8 is a flow chart of an exemplary comprehensive learning method according to the strategy of FIG. 7.

At step 800, an initial pulse sequence is used in an MR scanner 100 or Bloch simulator to generate an initial first signal and an initial second signal corresponding to first and second tissues S and S'.

At step 820, the processor 920 accesses MR data representing the first MR signal corresponding to a first tissue type and the second MR signal corresponding to a second tissue type.

At step 804, a reinforcement learning method is performed in the ANN to learn a signal evolution function to be applied by the ANN.

At step 806 the MR data are converted into data representing third and fourth signals in a second signal space. The conversion may be performed by an autoencoder. The conversion can apply different weights for different points in time.

At step 808, the ANN performs metric learning to learn a conversion to maximize a distance between the third signals and fourth signals, and minimize intra-class distance among fourth signals.

At step 810, a pulse sequence is learned, such that when an MR scanner applies the pulse sequence to tissues of the first tissue type and the second tissue type, a first signal corresponding to the first tissue type and a second signal corresponding to the second tissue type are generated, and a difference between the first signal and the second signal is maximized.

The design of the sequence can be solved by a specific designed learning strategy. The learning strategy is based on metric learning can be applied for a time evolving sequence. For example, the comprehensive learning method is advantageous for images acquired in partial volume, perfusion or diffusion testing.

Thus, a comprehensive learning model combines reinforcement learning and metric learning.

A comprehensive learning model learns the sequence through a metric learning process and including explicitly modeled MR pulse sequence within the ANN.

Using the proposed learning strategy, the sequence design goal can be set to maximize the contrast in the images.

Using the proposed learning strategy, the sequence is learned directly through the learning.

The signal X can be further modeled to include physiological effects such as partial volume, perfusion, diffusion and the like.

The difference between signals and tissues can be defined using various types of metrics, including but not limited to l1, l2 and etc.

The sequence design task under the proposed invention scheme can be application oriented. The image contrast to be maximized can be selected in specific application according to scanning needs. Examples include to maximize pathology contrast, to maximize grey and white matter contrast, to maximize contrast enhanced and unenhanced contrast and etc.

The methods and system described herein may be at least partially embodied in the form of computer-implemented processes and apparatus for practicing those processes. The disclosed methods may also be at least partially embodied in the form of tangible, non-transitory machine readable storage media encoded with computer program code. The media may include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods may also be at least partially embodied in the form of a computer into which computer program code is loaded and/or executed, such that, the computer becomes a special purpose computer for practicing the methods. When implemented on a general-purpose processor, the computer program code segments configure the processor to create specific logic circuits. The methods may alternatively be at least partially embodied in a digital signal processor formed of application specific integrated circuits for performing the methods.

Although the subject matter has been described in terms of exemplary embodiments, it is not limited thereto. Rather, the appended claims should be construed broadly, to include other variants and embodiments, which may be made by those skilled in the art.

What is claimed is:

1. A method for using an artificial neural network (ANN) to automatically produce a magnetic resonance (MR) imaging pulse sequence, the method comprising:
    (a) identifying a first MR signal corresponding to a first tissue and a second MR signal corresponding to a second tissue,
    (b) selecting an RF pulse to be applied to the first tissue and the second tissue;
    (c) based on at least the first MR signal, the second MR signal, and the RF pulse determining an updated first MR signal and an updated second MR signal;
    (d) computing a difference between the updated first signal and the updated second MR signal;
    (e) adding the difference to an accumulated difference;
    (f) repeating steps (b) to (e) one or more times;
    (g) controlling the ANN to use reinforcement learning to select the MR imaging pulse sequence based, at least in part, on the accumulated difference.

2. The method of claim 1, wherein step (c) includes using a Bloch simulator to compute the updated first MR signal and the updated second MR signal.

3. The method of claim 1, wherein step (g) selects the MR imaging pulse sequence so as to maximize the accumulated difference given a fixed length of the MR imaging pulse sequence.

4. The method of claim 1, wherein step (g) selects the MR imaging pulse sequence so as to minimize a length of the MR imaging pulse sequence given a fixed value of the accumulated difference.

5. The method of claim 1, wherein the updated first MR signal and the updated second MR signal are further based on at least one of the group consisting of a partial volume parameter, a perfusion parameter, and a diffusion parameter.

6. The method of claim 1, wherein step (c) computes the updated first MR signal and the updated second MR signal based on a rate of longitudinal relaxation of the first tissue or the second tissue that changes over time or a rate of transverse relaxation of the first tissue or the second tissue that varies over time.

7. The method of claim 1, wherein each time step (d) is executed, a respectively different discount factor is applied to the difference before adding the difference to the accumulated difference.

8. The method of claim 1, wherein step (c) includes:
    applying the RF pulse to the first tissue and the second tissue, and
    measuring the updated first MR signal and the updated second MR signal using the MRI scanner.

9. A method for using an artificial neural network (ANN) to automatically produce a magnetic resonance (MR) imaging pulse sequence, the method comprising:
    (a) accessing data representing a first MR signal in a first signal space corresponding to a first tissue type and a second MR signal in the first signal space corresponding to a second tissue type;

(b) converting the data into data representing a third signal and a fourth signal in a second signal space; and (c) using the ANN to perform metric learning so as to learn a conversion from the first signal space to the second signal space to be used in step (b), such that a distance between the third signal and the fourth signal in the second signal space is maximized; and (d) computing a pulse sequence, such that when an MR scanner applies the pulse sequence to tissues of the first tissue type and the second tissue type, the third and fourth signals are generated in the second signal space.

10. The method of claim 9, wherein step (d) uses machine learning to compute the pulse sequence.

11. The method of claim 9, further comprising, before step (a):

using an initial pulse sequence in the MR scanner to generate the first MR signal and the second MR signal, wherein the pulse sequence computed in step (d) is different from the initial pulse sequence.

12. The method of claim 9, wherein the conversion is selected to minimize intra-class distance among third signals corresponding to the first tissue type and minimize intra-class distance among fourth signals corresponding to the second tissue type.

13. The method of claim 9, wherein the data correspond to two or more different points in time, and the conversion includes applying respectively different weights to data from different points in time.

14. The method of claim 9, wherein the ANN used in step (c) is an autoencoder.

15. The method of claim 9, wherein step (c) includes performing dimensionality reduction on a number of variables considered in computing the pulse sequence.

16. A non-transitory, machine readable storage medium encoded with computer program code for programming a processor to perform a method to automatically produce a magnetic resonance (MR) imaging pulse sequence and signal evolution using an artificial neural network (ANN), the method comprising:

(a) accessing data representing a first MR signal corresponding to a first tissue type and a second MR signal corresponding to a second tissue type;

(b) performing a reinforcement learning method in the ANN to learn a signal evolution function to be applied by the ANN; and (c) using the ANN to perform metric learning so as to learn a pulse sequence, such that when an MR scanner applies the pulse sequence to tissues of the first tissue type and the second tissue type, a first signal corresponding to the first tissue type and a second signal corresponding to the second tissue type are generated, and a difference between the first signal and the second signal is maximized.

17. An artificial neural network (ANN) for automatically generating a magnetic resonance (MR) imaging pulse sequence, the ANN configured to:

(a) identify a first MR signal corresponding to a first tissue and a second MR signal corresponding to a second tissue, (b) select an RF pulse to be applied to the first tissue and the second tissue;

(c) based on at least the first MR signal, the second MR signal, and the RF pulse determine an updated first MR signal and an updated second MR signal;

(d) compute a difference between the updated first signal and the updated second MR signal;

(e) add the difference to an accumulated difference;

(f) repeat steps (b) to (e) one or more times; and (g) use reinforcement learning to select the MR imaging pulse sequence based, at least in part, on the accumulated difference.

* * * * *